US007186402B2

(12) United States Patent
Duan et al.

(10) Patent No.: US 7,186,402 B2
(45) Date of Patent: Mar. 6, 2007

(54) MEDICINAL AEROSOL COMPOSITIONS WITH AN AMIDE AND/OR ESTER CONTAINING EXCIPIENT COMPOUND

(75) Inventors: Daniel C. Duan, St. Paul, MN (US); Robert A. Scherrer, White Bear Lake, MN (US); James S. Stefely, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 67 days.

(21) Appl. No.: 10/327,198

(22) Filed: Dec. 20, 2002

(65) Prior Publication Data

US 2003/0138381 A1 Jul. 24, 2003

Related U.S. Application Data

(60) Provisional application No. 60/342,623, filed on Dec. 21, 2001.

(51) Int. Cl.
*A61K 9/00* (2006.01)
*A61K 9/12* (2006.01)
*A61K 9/14* (2006.01)

(52) U.S. Cl. ............................ 424/45; 424/43; 424/46; 514/958

(58) Field of Classification Search .................. 424/45, 424/46, 434, 489, 421, 78.17, 43; 514/2, 514/3, 958

See application file for complete search history.

(56) References Cited

U.S. PATENT DOCUMENTS

| | | | | |
|---|---|---|---|---|
| 5,225,183 | A | 7/1993 | Purewal et al. | |
| 5,492,688 | A | 2/1996 | Byron et al. | |
| 5,508,023 | A | 4/1996 | Byron et al. | |
| 5,569,450 | A | 10/1996 | Duan et al. | |
| 5,676,930 | A | 10/1997 | Jager et al. | |
| 5,676,931 | A | 10/1997 | Adjei et al. | |
| 5,770,559 | A | 6/1998 | Manning et al. | |
| 6,042,811 | A | 3/2000 | Duan et al. | |
| 6,126,919 | A | 10/2000 | Stefely et al. | |
| 6,136,294 | A | 10/2000 | Adjei et al. | |
| 6,218,353 | B1 | 4/2001 | Romack et al. | |
| 6,258,857 | B1 * | 7/2001 | Iijima et al. | 516/1 |
| 6,284,749 | B1 | 9/2001 | Castello et al. | |
| 2003/0138381 | A1 | 7/2003 | Duan et al. | |
| 2003/0147814 | A1 * | 8/2003 | Scherrer et al. | 424/45 |
| 2003/0152521 | A1 * | 8/2003 | Stefely et al. | 424/45 |

FOREIGN PATENT DOCUMENTS

| | | |
|---|---|---|
| WO | WO 94/08599 | 4/1994 |
| WO | WO 94/13263 | 6/1994 |
| WO | WO 94/21229 | 9/1994 |
| WO | WO 96/19197 | 6/1996 |
| WO | WO 96/30036 | 10/1996 |
| WO | WO 00/16814 | 3/2000 |
| WO | WO 01/93835 | 12/2001 |

OTHER PUBLICATIONS

Jashnani, R.N., Dalby, R.N., Byron, P.R., “Preparation, Characterization, and Dissolution Kinetics of Two Novel Albuterol Salts”, J. Pharm. Sci., 82(6), p. 613-616.

Berg, S.M., Bighley, L.D., Monkhouse, D.C., “Pharmaceutical Salts”, J. Pharm. Sci., 66(1), p. 1-19.

Meakin, B.J., D.A. Lewis, D. Ganderton, and G. Brambilla (2000) “Countering Challenges Posed by Mimicry of CFC Performance Using HFA Systems”, in proceedings of Respiratory Drug Delivery VII, R. Dalby, P. Byron, S. Farr, and J. Peart, editors. Serentec Press, Inc., Raleigh, NC.

Brambilla, G., D. Ganderton, R. Garzia, D. Lewis, B. Meakin, P. Ventura (1999). “Modulation of Aerosol Clouds Produced by Pressurised Inhalation Aerosols”, International Journal of Phamraceutics, 186:53-61.

Stefely J, Duan D, Myrdal P, Ross D, Schultz D, and Leach C L (2000) “Design and Utility of a novel class of biocompatible excipients for HFA-based MDIs”. Respiratory Drug Delivery VII, 82-90.

* cited by examiner

*Primary Examiner*—Johann Richter
*Assistant Examiner*—Mina Haghighatian
(74) *Attorney, Agent, or Firm*—Ted Ringsred

(57) ABSTRACT

The invention comprises a medicinal aerosol composition comprising a propellant, an excipient comprising an acid or amine end-group and at least one and no more than two amide and/or ester functional groups, and a drug. The invention also comprises particulate medicinal compositions comprising particles with a mean mass aerodynamic diameter of less than about 10 microns that incorporate an excipient containing an acid or amine end-group and at least one and no more than two amide and/or ester functional groups.

12 Claims, No Drawings

US 7,186,402 B2

MEDICINAL AEROSOL COMPOSITIONS WITH AN AMIDE AND/OR ESTER CONTAINING EXCIPIENT COMPOUND

This application claims benefit of priority to provisional patent application 60/342,623, filed Dec. 21, 2001.

FIELD

The present invention relates to medicinal aerosol compositions and products, and, in particular, to excipients for use in such compositions and products.

BACKGROUND OF THE INVENTION

The delivery of a therapeutically active compound (i.e., a drug) to a living organism is generally affected by a number of parameters beyond the actual chemical identity and pharmacological activity of the drug.

Medicinal aerosols can be an effective way to introduce a drug into the pulmonary system via oral or nasal inhalation, but there are a number of important parameters governing medicinal aerosol compositions that affect their performance. The relative importance of these parameters can vary depending on the type of dosage form used (e.g., metered dose inhaler or MDI, dry powder inhaler, nebulizer) and the type of drug being delivered, but will usually include such things as the concentration of drug in the dosage form, the particle size of the aerosol that is delivered to an organism, the physicochemical stability of the composition, and the ability of particles delivered to the pulmonary system to be absorbed by the body.

In order to achieve certain desirable properties or an acceptable balance of properties it is sometimes desirable to incorporate various excipients into a medicinal aerosol composition. As used in this application, an "excipient" refers broadly to any formulation additive other than the primary active drug moiety used to improve some aspect of the formulation. Many different excipients have been suggested for use in medicinal aerosols, for such things as solubilizing drug, physically stabilizing dispersion of particles, increasing the emitted particle size, and so on. But many proposed excipients, while perhaps providing one or more benefits, suffer from drawbacks that make them otherwise undesirable for use, such as toxicological problems, manufacturing difficulties, limited solubility or detrimental interactions with other product components. Hence, there is an ongoing need for new and effective excipients that are useful in medicinal aerosols, particular pressurized medicinal aerosols using hydrofluorocarbon propellants, such as HFC-134a and HFC-227. Although tremendous research investment has been made over the last decade, formulating CFC-free pressurized metered dose inhalers that are suitable in terms of the stringent functional and therapeutic requirements today continues to be of major importance.

SUMMARY OF THE INVENTION

It has now been found that certain compounds having at least one, but not more than two, amide and/or ester functional group(s) are particularly useful as medicinal aerosol excipients. The present invention provides a medicinal aerosol composition comprising a propellant, an excipient comprising a compound of the structure X—$R_1$—Y-Z, and a drug. X is selected from the group consisting of: —C(O)OH; —$S(O_2)$OH; —$OS(O_2)$OH; —$P(OH)_2$O; —$OP(OH)_2$O; and —$N(R_2)(R_2)$. Y is selected from the group consisting of: —C(O)O—; —OC(O)—; —C(O)—$NR_4$—; and —$NR_4$—C(O)—. Z is —$R_3$ or —$R_1$—Y—$R_3$. Each $R_1$ is independently a linear, branched, or cyclic hydrocarbon with 1 to 22 carbons, which may be optionally interrupted by an —O—, —S—, —$N(R_4)$—, ester, or amide group, or may be optionally substituted by one or more substituents selected from the group consisting of: —OH; —SH; —C(O)OH; and —$N(R_4)(R_4)$. Each $R_2$ is independently selected from hydrogen or linear, branched, or cyclic hydrocarbon with 1 to 18 carbons, which may be optionally interrupted by an —O—, —S—, or —$N(R_4)$— group, or may be optionally substituted by one or more substituents selected from the group consisting of: —OH; —SH; and —$N(R_4)(R_4)$. $R_3$ is a linear, branched, or cyclic hydrocarbon with 1 to 20 carbons, which may be optionally interrupted by an —O—, —S—, or —$N(R_4)$— group, or may be optionally substituted by one or more substituents selected from the group consisting of: —OH; —SH; and —$N(R_4)(R_4)$. Each $R_4$ is independently selected from hydrogen or a linear, branched, or cyclic hydrocarbon with 1 to 18 carbons. $R_1$ and $R_4$ may optionally be connected together to form an alkylene bridge of from 2 to 4 carbons. The compound has no more than two amide and/or ester functional groups.

In a preferred embodiment, the compositions of the invention are solutions containing hydrofluorocarbon propellant, preferably HFC-134a and/or HFC-227, although other propellants are also suitable.

In another aspect, the present invention provides a particulate medicinal composition comprising particles incorporating a drug and an excipient comprising a compound of the structure X—$R_1$—Y-Z, wherein the particles have a mass mean aerodynamic diameter of less than about 10 microns. X is selected from the group consisting of: —C(O)OH; —$S(O_2)$OH; —$OS(O_2)$OH; —$P(OH)_2$O; —$OP(OH)_2$O; and —$N(R_2)(R_2)$. Y is selected from the group consisting of: —C(O)O—; —OC(O)—; —C(O)—$NR_4$—; and —$NR_4$—C(O)—. Z is —$R_3$ or —$R_1$—Y—$R_3$. Each $R_1$ is independently a linear, branched, or cyclic hydrocarbon with 1 to 22 carbons, which may be optionally interrupted by an —O—, —S—, —$N(R_4)$—, ester, or amide group, or may be optionally substituted by one or more substituents selected from the group consisting of: —OH; —SH; —C(O)OH; and —$N(R_4)(R_4)$. Each $R_2$ is independently selected from hydrogen or linear, branched, or cyclic hydrocarbon with 1 to 18 carbons, which may be optionally interrupted by an —O—, —S—, or —$N(R_4)$— group, or may be optionally substituted by one or more substituents selected from the group consisting of: —OH; —SH; and —$N(R_4)(R_4)$. $R_3$ is a linear, branched, or cyclic hydrocarbon with 1 to 20 carbons, which may be optionally interrupted by an —O—, —S—, or —$N(R_4)$— group, or may be optionally substituted by one or more substituents selected from the group consisting of: —OH; —SH; and —$N(R_4)(R_4)$. Each $R_4$ is independently selected from hydrogen or a linear, branched, or cyclic hydrocarbon with 1 to 18 carbons. $R_1$ and $R_4$ may optionally be connected together to form an alkylene bridge of from 2 to 4 carbons. The compound has no more than two amide and/or ester functional groups.

In a preferred embodiment of this aspect of the invention the drug and excipient form a hydrophobic ion pair complex. In another preferred embodiment of this aspect of the invention the drug and excipient form a pharmaceutical salt.

In still another aspect, the present invention provides a medicinal aerosol composition comprising a propellant, an excipient that comprises an acid or amine end-group and at least one and no more than two amide and/or ester functional groups, and a drug, where the drug, excipient, and propellant form a solution.

DETAILED DESCRIPTION OF THE INVENTION

The present invention comprises a medicinal aerosol composition comprising a propellant, an excipient comprising a compound of the structure X—$R_1$—Y-Z, and a drug.

Suitable propellants include, for example, a chlorofluorocarbon (CFC), such as trichlorofluoromethane (also referred to as propellant 11), dichlorodifluoromethane also referred to as propellant 12), and 1,2-dichloro-1,1,2,2-tetrafluoroethane (also referred to as propellant 114), a hydrochlorofluorocarbon, a hydrofluorocarbon (HFC), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, butane, propane, or mixtures thereof. Preferably, the propellant includes a hydrochlorofluorocarbon, a hydrofluorocarbon, or mixtures thereof. More preferably, a hydrofluorocarbon is used as the propellant. Most preferably, HFC-227 and/or HFC-134a are used as the propellant. The propellant is preferably present in an amount sufficient to propel a plurality of doses of the drug from an aerosol canister, preferably a metered dose inhaler.

Suitable excipients comprise compounds of the structure X—$R_1$—Y-Z.

X is selected from the group consisting of: —C(O)OH; —S(O₂)OH; —OS(O₂)OH; —P(OH)₂O; —OP(OH)₂O; and —N($R_2$)($R_2$), and more preferably is —C(O)OH.

Each $R_1$ is independently a linear, branched, or cyclic hydrocarbon with 1 to 22 carbons, which may be optionally interrupted by an —O—, —S—, —N($R_4$)—, ester, or amide group, or may be optionally substituted by one or more substituents selected from the group consisting of: —OH; —SH; —C(O)OH; and —N($R_4$)($R_4$). Preferably, $R_1$ is a linear, branched, or cyclic hydrocarbon with 1 to 22 carbons, more preferably 1 to 6 carbons, and most preferably with 1 to 2 carbons, which may be optionally interrupted by an —O— group. More preferably, $R_1$ is a linear, branched, or cyclic hydrocarbon with 1 to 22 carbons, more preferably 1 to 6 carbons, and most preferably with 1 to 2 carbons.

Y is selected from the group consisting of: —C(O)O—; —OC(O)—; —C(O)—N($R_4$)—; and —N($R_4$)—C(O)—.

Z is —$R_3$ or —$R_1$—Y—$R_3$, and more preferably is $R_3$.

Each $R_2$ is independently selected from hydrogen or linear, branched, or cyclic hydrocarbon with 1 to 18 carbons, preferably 1 to 12 carbons, more preferably 1 to 4 carbons, and most preferably 1 carbon, which may be optionally interrupted by an —O—, —S—, or —N($R_4$)— group, or may be optionally substituted by one or more substituents selected from the group consisting of: —OH; —SH; and —N($R_4$)($R_4$). Preferably, each $R_2$ is independently a linear, branched, or cyclic hydrocarbon with 1 to 18 carbons, which may be optionally interrupted by an —O— group. More preferably, each $R_2$ is independently a linear, branched, or cyclic hydrocarbon with 1 to 18 carbons, preferably 1 to 12 carbons, more preferably 1 to 4 carbons, and most preferably 1 carbon, $R_3$ is a linear, branched, or cyclic hydrocarbon with 1 to 20 carbons, more preferably 6 to 20 carbons, and most preferably with 10 to 18 carbons, which may be optionally interrupted by an —O—, —S—, or —N($R_4$)— group, or may be optionally substituted by one or more substituents selected from the group consisting of: —OH; —SH; and —N($R_4$)($R_4$). Preferably, $R_3$ is a linear, branched, or cyclic hydrocarbon with 1 to 20 carbons, more preferably 6 to 20 carbons, and most preferably with 10 to 18 carbons.

Each $R_4$ is independently selected from hydrogen or a linear, branched, or cyclic hydrocarbon with 1 to 18 carbons, more preferably 1 to 4 carbons, and most preferably is methyl. $R_1$ and $R_4$ may optionally be connected together to form an alkylene bridge of from 2 to 4 carbons.

Hydrocarbons of $R_1$, $R_2$, $R_3$, $R_4$ may be saturated or unsaturated.

Unlike certain known excipients, the compounds of the present invention have no more than two amide and/or ester functional groups (in other words, one amide, two amides, one ester, two esters, or one amide and one ester).

Preferred acid-containing excipients include acylated endogenous acids, including taurine and alpha-amino acids, such as alanine, proline, and sarcosine, and hydroxy acids, such as glycolic acid, lactic acid, and isethionic acid. Preferred amine-containing excipients include hindered or tertiary amines, more preferably esterified alpha-amino acids, or esterified alpha-amino acid derivatives, such as dimethylglycine. Especially preferred are acylated sarcosines, for example cocoyl sarcosine and stearoyl sarcosine. Preferred excipients are biocompatible.

In a preferred embodiment, the excipient contains two amide and/or ester groups. Preferred examples of excipients containing two amide and/or ester groups with acid functionality include diacylated serine or threonine; diesters of sulfosuccinic acid; mono-reaction products of diacids, such as diglycolic acid or succinic acid with alkyl lactates or esterified a-amino acids, such as lauryl lactate or dodecyl sarcosine; and reaction products of acylated aminoacids, such as acylated sarcosine with a hydroxy or amino acid, such as methyl taurine or lactic acid. Preferred examples of diester/amides with amine functionality include diesters of glutamic or aspartic acid; reaction product of acylated amino/hydroxy acids with N,N-dimethyl ethanol amine; and reaction product of esterified amino/hydroxy acids, such as lauroyl lactylate with dimethyl glycine.

Among the advantages of these excipients is the ability to increase the solubility of amine- or acid-containing drugs in HFC propellant systems. Preferably, drug solubility can be increased due to the formation of ion pair complexes. The ability of these excipients to increase drug solubility in metered dose inhalers above that achievable with the use of low- or semi-volatile cosolvents alone can also allow for delivery of a unique combination of high respirable fraction (i.e., the fraction of total particles emitted from the actuator mouth piece having a aerodynamic particle size of less than about 5 microns) along with a large respirable mass, which is highly desirable and normally do not occur simultaneously. Proper selection of the fatty, acid chain length may also allow controlled or sustained release of the drug. These excipients can also be used as suspension aids in suspension metered dose inhalers.

Medicinal formulations according to the present invention contain a drug either dispersed or dissolved in the formulation in a therapeutically effective amount. As used herein the term "therapeutically effective amount" means an amount sufficient to induce a therapeutic effect, such as bronchodilation or antiviral activity. The amount will vary according to factors known to those skilled in the art, such as the pharmacological activity of the particular drug, the condition being treated, the frequency of administration, the treatment site, and any other therapeutic agents being coadministered.

As used herein, the term "drug," includes its equivalents, "bioactive agent," and "medicament" and is intended to have its broadest meaning as including substances intended for use in the diagnosis, cure, mitigation, treatment or prevention of disease, or to affect the structure or function of the body. The drugs can be neutral or ionic. Preferably, they are suitable for oral and/or nasal inhalation. Delivery to the respiratory tract and/or lung, in order to effect bronchodilation and to treat conditions such as asthma and chronic obstructive pulmonary disease, is preferably by oral inhalation. Alternatively, to treat conditions such as rhinitis or allergic rhinitis, delivery is preferably by nasal inhalation.

Suitable drugs include, for example, antiallergics, anticancer agents, antifungals, antineoplastic agents, analgesics, bronchodilators, antihistamines, antiviral agents, antitussives, anginal preparations, antibiotics, anti-inflammatories, immunomodulators, 5-lipoxygenase inhibitors, leukotriene antagonists, phospholipase $A_2$ inhibitors, phosphodiesterase IV inhibitors, peptides, proteins, steroids, and vaccine preparations. A group of preferred drugs include adrenaline, albuterol, atropine, beclomethasone dipropionate, budesonide, butixocort propionate, clemastine, cromolyn, epinephrine, ephedrine, fentanyl, flunisolide, fluticasone, formoterol, ipratropium bromide, isoproterenol, lidocaine, morphine, nedocromil, pentaridine isoethionate, pirbuterol, prednisolone, salmeterol, terbutaline, tetracycline, 4-amino-$\alpha,\alpha$-2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and mixtures thereof. Particularly preferred drugs include pirbuterol, 4-amino-$\alpha,\alpha$-2-trimethyl-1H-imidazo[4,5-c]quinoline-1-ethanol, 2,5-diethyl-10-oxo-1,2,4-triazolo[1,5-c]pyrimido[5,4-b][1,4]thiazine, 1-(1-ethylpropyl)-1-hydroxy-3-phenylurea, and pharmaceutically acceptable salts and solvates thereof, and mixtures thereof.

In a preferred embodiment the drug and excipient form a hydrophobic ion pair complex. To assist in the understanding of this preferred embodiment, but not to be bound by theory, it is believed that the drug and the excipient are associated in the form of a complex between the excipient and the drug. Preferably, the excipient and the drug have oppositely charged ionic portions which associate to form an ion pair (IP) complex. Preferably, the drug comprises a cationic portion that associates with the deprotonated form of the excipient. In the case where the excipient has a hydrophobic portion that does not interact with the drug, the ion pair complex can be referred to as a hydrophobic ion pair (HIP) complex. Hydrophobic ion pair (HIP) complexes are well known to one skilled in the art and are described in U.S. Pat. No. 5,770,559 (Manning, et al.), the disclosure of which is incorporated herein by reference.

For oral and/or nasal inhalation, formulations where the drug is in solution are generally preferred; however, if suspensions are used, preferably the drug is micronized (i.e., in the form of particles having a diameter on the order of micrometers). More preferably, a therapeutically effective fraction of the drug (typically, about 90% or more) is in the form of particles having a diameter of less than about 10 micrometers, and most preferably, less than about 5 micrometers. These particle sizes also apply for the formulations of drug and amide and/or ester containing excipient used in dry powder inhalers. This ensures that the drug can be inhaled into the respiratory tract and/or lungs. It will be recognized that such limitations do not necessarily exist for nasal inhalation.

Preferably, medicinal formulations according to the present invention include a drug in an amount and in a form such that the drug can be administered as an aerosol. More preferably, the drug is present in an amount such that the drug can produce its desired therapeutic effect with one or two doses from a conventional aerosol canister with a conventional valve, such as a metered dose valve. As used herein, an "amount" of the drug can be referred to in terms of quantity or concentration. A therapeutically effective amount of a drug can vary according to a variety of factors, such as the potency of the particular drug, the route of administration of the formulation, the mode of administration of the formulation, and the mechanical system used to administer the formulation. A therapeutically effective amount of a particular drug can be selected by those of ordinary skill in the art with consideration of such factors. Generally, a therapeutically effective amount will be from about 0.0001 parts to about 5 parts, more preferably from about 0.01 parts to about 1 part, by weight based on 100 parts of the medicinal formulation.

Medicinal formulations according to the present invention can include an optional cosolvent or mixtures of cosolvents. The cosolvent can be used in an amount effective to dissolve the drug and/or the excipient. Preferably, the cosolvent is used in an amount of about 0.01 to about 25% by weight, more preferably about 2 to about 15%, and most preferably about 4 to about 10%, based on the total weight of the formulation. Examples of suitable cosolvents include ethanol or isopropanol.

Medicinal formulations according to the present invention may be in the form of a suspension in propellant. Such suspensions will preferably include an amount of cosolvent that is sufficient to dissolve the amide and/or ester containing excipient, but that is not high enough to dissolve the suspended drug. The ratio of amide and/or ester containing excipient to drug in such suspensions is preferably between about 0.01 and 0.1 on a weight basis.

Other additives (i.e., excipients), such as lubricants, surfactants, and taste masking ingredients, can also be included in medicinal formulations of the present invention.

The amount of amide and/or ester containing excipient used will depend upon a number of factors, including the type and amount of drug used and the desired therapeutic effect. In a preferred embodiment the molar ratio of amide and/or ester containing excipient to drug will be between about 1.5:1 and 1:2, and more preferably will be about 1:1. The excipient and drug are preferably present as a pharmaceutical salt or hydrophobic ion pair.

Medicinal compositions of the present invention can be useful in providing sustained release of a drug to the body. Such compositions include a drug and a sufficient amount of amide and/or ester containing excipient which when delivered is associated with the drug (e.g., drug entrapped/encapsulated in an excipient matrix or as a drug-excipient salt) so as to provide for sustained release of the drug. When such medicinal aerosol compositions are administered to the body the drug is released in a sustained manner over a period ranging, for example, from about 30 minutes to a day or more. The time period for release of the drug depends upon many factors including, for example, the amount and type of amide and/or ester containing excipient used, and the chemical and physical nature of the drug. The amount of excipient that will be sufficient to provide a desired sustained release profile may be determined on a case-by-case basis with little difficulty. Preferably, the amide and/or ester containing excipient is present in an amount such that the period of therapeutic activity of the drug is increased by a factor of at least about 1.5 relative to the period of activity of the same formulation with respect to the propellant and drug but without the excipient.

Conventional aerosol canisters, such as those of aluminum, glass, stainless steel, or polyethylene terephthalate, can be used to contain the medicinal formulations according to the present invention. Aerosol canisters equipped with conventional valves, preferably, metered dose valves, can be used to deliver the formulations of the invention. The selection of the appropriate valve assembly typically depends on the components in the medicinal formulation.

Preparation of the compositions may be by a variety of conventional methods. Where a cosolvent is used, a mixture of drug, excipient, and cosolvent may be prepared, to which propellant is subsequently added to prepare a metered dose inhaler. Alternatively, drug and excipient may be dissolved in a process solvent and recrystallized to prepare a pharmaceutical salt.

In another aspect, the present invention comprises a particulate medicinal composition comprising particles incorporating a drug and an excipient comprising a compound of the structure X—$R_1$—Y-Z, where X, $R_1$, Y, and Z are as described above, and where the, particles have a mass mean aerodynamic diameter (MMAD) of less than about 10 microns, and more preferably less than about 5 microns. The mean diameter of the particles is preferably less than about 5 microns. In another preferred embodiment the drug and excipient form a pharmaceutical salt.

Particulate medicinal compositions of the present invention may be particularly useful in dry powder inhalers or suspension-based metered dose inhalers.

In still another aspect, the present invention comprises a medicinal aerosol formulation comprising a propellant, an excipient that comprises an acid or amine end-group and at least one and no more than two amide and/or ester functional groups, and a drug, where the drug, excipient, and propellant form a solution. Acid end-groups are preferably carboxylic acids, sulfuric acids, or sulfonic acids. Amine end groups are disubstituted where the substituents are independently hydrogen or a linear, branched or cyclic alkane with 1 to 18 carbons, and preferably a linear, branched or cyclic alkane with 1 to 4 carbons. Preferably, the medicinal aerosol formulation further comprises a polar cosolvent.

Preferred acid-containing excipients include acylated endogenous acids, including taurine and alpha-amino acids, such as alanine, proline, and sarcosine. Preferred amine-containing excipients include hindered or tertiary amines, more preferably esterified alpha-amino acids or their derivatives, such as dimethylglycine. Especially preferred are acylated sarcosines, for example cocoyl sarcosine and stearoyl sarcosine. Preferred excipients are biocompatible.

EXAMPLES

Examples 1 to 5

A drug (4-amino-2-ethoxymethyl-α,α-dimethyl-1H-imidazo[4,5-c]quinoline-1-ethanol), lauroyl sarcosine (available as Hamposyl L, a trademark of Hampshire Chemicals), and ethanol were added to a canister which was capped with a continuous valve. HFC-134a propellant was added to the canister and mixed together to form a solution formulation. The relative weight percentages of excipient and ethanol are shown below in table 1. An excess of drug was provided. The canister was shaken for at least two days. A continuous valve was crimped onto a second, empty canister, which was chilled by being placed on dry ice. The formulation from the first canister was passed through a 0.22 micron filter, and into the second canister by depressing both continuous valves. The vapor pressure of the formulation in the first canister caused the formulation to flow through the filter. The solubility of the drug is taken as the concentration of drug in the solution that passes through the filter and into the second canister. The solution drug concentration was assayed for drug concentration using an ion exchange HPLC method with external standard quantitation and UV detection at 247 nm.

The drug solubility is shown below in table 1.

TABLE 1

| Example Number | lauroyl sarcosine (% w/w) | Ethanol (% w/w) | Drug Solubility (% w/w) |
|---|---|---|---|
| 1 | 0.10 | 5.11 | 0.14 |
| 2 | 0.10 | 15.33 | 0.42 |
| 3 | 0.53 | 10.27 | 0.77 |
| 4 | 1.12 | 5.31 | 0.08 |
| 5 | 0.99 | 14.97 | 1.41 |

Examples 6 to 10

A series of formulations were prepared following the method of examples 1 to 5, with the exception that lauroyl lactylate was used in place of lauroyl sarcosine. The relative weight percentages of each component and the drug solubility are shown below in table 2.

TABLE 2

| Example Number | lauroyl lactylate (% w/w) | Ethanol (% w/w) | Drug Solubility (% w/w) |
|---|---|---|---|
| 6 | 0.10 | 5.00 | 0.13 |
| 7 | 0.09 | 14.90 | 0.36 |
| 8 | 0.50 | 9.98 | 0.58 |
| 9 | 1.00 | 5.01 | 0.14 |
| 10 | 0.99 | 15.19 | 1.42 |

Examples 11 to 13

A series of formulations were prepared following the method of examples 1 to 5, with the exception that myristoyl sarcosine was used in place of lauroyl sarcosine. The relative weight percentages of each component and the drug solubility are shown below in table 3.

TABLE 3

| Example Number | myristoyl sarcosine (% w/w) | Ethanol (% w/w) | Drug Solubility (% w/w) |
|---|---|---|---|
| 11 | 1.07 | 5.000 | 0.08 |
| 12 | 0.53 | 10.00 | 0.72 |
| 13 | 0.94 | 14.26 | 1.22 |

Examples 14 to 16

A series of formulations were prepared following the method of examples 1 to 5, with the exception that steroyl sarcosine was used in place of lauroyl sarcosine. The relative weight percentages of each component and the drug solubility are shown below in table 4.

TABLE 4

| Example Number | steroyl sarcosine (% w/w) | Ethanol (% w/w) | Drug Solubility (% w/w) |
| --- | --- | --- | --- |
| 14 | 1.05 | 5.17 | 0.02 |
| 15 | 0.51 | 9.95 | 0.20 |
| 16 | 1.00 | 15.00 | 1.02 |

Example 17

Lauroyl sarcosine (3.80 grams, available as Hamposyl L, a trademark of Hampshire Chemicals) was dissolved in 30 mL of warm ethyl acetate and filtered to remove a small amount of insoluble material. A drug, 4-amino-2-ethoxymethyl-α,α-dimethyl-1H-imidazo[4,5-c]quinoline-1-ethanol (4.00 grams), was added to and dissolved in the filtrate upon warming. Addition of 10 ml of hexane caused the formation of a crystal mass on standing at room temperature and then under refrigeration. The crystals were washed twice by cold ethyl acetate/hexane 1:1 (v:v) followed by hexane to obtain 7.17 g crystals with a melting point of 107.5–109° C. No lauric acid was detected by mass spectrometry. This product was recrystallized from 70 mL ethyl acetate and 30 mL of hexane resulting in 6.73 grams of white crystals with a melting point of 107–108° C.

Example 18

1-isobutyl-2-(2-methoxyethyl)-1H-imidazo[4,5-c]quinolin-4-amine (0.0115 grams), lauroyl sarcosine (0.0104 grams, available as Hamposyl L, a trademark of Hampshire Chemicals), and ethanol (1.2885 grams) were added to a canister which was capped with a continuous valve. HFC-134a propellant (12.0 grams) was added to the canister and mixed together to form a solution formulation. The contents of the canister were chilled and transferred to a 15 mL canister and a 50 microliter Spraymiser (trademark of 3M Co.) valve was crimped onto the canister. The canister was placed into a standard solution MDI actuator with an orifice diameter of approximately 0.30 mm.

Efficacy for this formulation was determined using an asthma sephadex rat model, which is described in U.S. Pat. No. 6,039,969 (Tomai, et al.), the disclosure of which is incorporated herein by reference. Efficacy is expressed as a percent inhibition of eosinophils in the lung. This formulation provided 62% eosinophils inhibition.

Examples 19 to 32

Albuterol base, a sarcosine-derived amide bearing excipient, and ethanol were added to a canister which was capped with a continuous valve. HFA-134a propellant was added to the canister and mixed together to form a solution formulation. An excess of drug was provided. The canister was shaken for at least two days. A continuous valve was crimped onto a second, empty canister, which was chilled by being placed on dry ice. The formulation from the first canister was passed through a 0.22 micron filter, and into the second canister by depressing both continuous valves. The vapor pressure of the formulation in the first canister caused the formulation to flow through the filter and into the second canister. The solution drug concentration was assayed for drug concentration using a reverse phase HPLC with external standard quantitation and UV detection at 225 nm with a mobile phase of 55 parts 0.1% o-phosphoric acid: 45 parts methanol (v/v). The solubility of the drug is taken as the concentration of drug in the solution that passes through the filter and into the second canister. The resulting solubilities are shown in Table 5.

TABLE 5

| Example Number | Ethanol (% w/w) | Acyl sarcosine, (carbons chain length) | Acyl Sarcosine (% w/w) | Albuterol base solubility (% w/w) |
| --- | --- | --- | --- | --- |
| 19 | 15.2 | 6 | 3.3 | 2.49 |
| 20 | 15 | 8 | 3.1 | 2.37 |
| 21 | 15.7 | 10 | 3.3 | 2.00 |
| 22 | 15 | 4 | .98 | 1.70 |
| 23 | 14.9 | 6 | 1.06 | 1.48 |
| 24 | 15.2 | 8 | 1.25 | 1.16 |
| 25 | 14.8 | 10 | 1.27 | 1.47 |
| 26 | 15.3 | 12 | 1.0 | 1.84 |
| 27 | 15.1 | 14 | 0.98 | 0.93 |
| 28 | 14.7 | 18 | 0.98 | 0.66 |
| 29 | 10 | 4 | 0.54 | 0.76 |
| 30 | 10.2 | 6 | 1.0 | 1.03 |
| 31 | 9.9 | 8 | 1.1 | 0.77 |
| 32 | 9.9 | 10 | 1.3 | 0.56 |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A medicinal aerosol composition comprising:
   a propellant comprising a hydrofluorocarbon selected from the group consisting of 1,1,1,2-tetrafluoroethane, 1,1,1,2,3,3,3-heptafluoropropane, and a mixture thereof;
   an excipient comprising a compound of the structure X—$R_1$—Y-Z; wherein
   X is selected from the group consisting of: —C(O)OH; —S($O_2$)OH; —OS($O_2$)OH; —P(OH)$_2$O; —OP(OH)$_2$O; and —N($R_2$)($R_2$);
   Y is selected from the group consisting of: —C(O)O—; —OC(O)—; —C(O)—N($R_4$)—; and —N($R_4$)—C(O)—;
   Z is —$R_3$ or —$R_1$—Y—$R_3$;
   each $R_1$ is independently a linear, branched, or cyclic hydrocarbon with 1 to 22 carbons, which may be optionally interrupted by an —O—;
   each $R_2$ is independently selected from hydrogen or linear, branched, or cyclic hydrocarbon with 1 to 18 carbons, which may be optionally interrupted by an —O—, —S—, or —N($R_4$)— group, or may be optionally substituted by one or more substituents selected from the group consisting of: —OH; —SH; and —N($R_4$)($R_4$);
   $R_3$ is a linear, branched, or cyclic hydrocarbon with 1 to 20 carbons, which may be optionally interrupted by an —O—, —S—, or —N($R_4$)— group, or may be optionally substituted by one or more substituents selected from the group consisting of: —OH; —SH; and —N($R_4$)($R_4$);

Each $R_4$ is independently selected from hydrogen or a linear, branched, or cyclic hydrocarbon with 1 to 18 carbons;

wherein $R_1$ and $R_4$ may optionally be connected together to form an alkylene bridge of from 2 to 4 carbons; and wherein the compound has no more than two amide and/or ester functional groups; and a drug.

2. The medicinal aerosol composition of claim 1 wherein Z is $R_3$.

3. The medicinal aerosol composition of claim 2 wherein Y is selected from the group consisting of: —C(O)—N($R_4$)—; and —N($R_4$)—C(O)—.

4. The medicinal aerosol composition of claim 2 wherein Y is selected from the group consisting of: —C(O)O—; —OC(O)—.

5. The medicinal aerosol composition of claim 1 wherein Z is —$R_1$—Y—$R_3$.

6. The medicinal aerosol composition of claim 1 wherein the drug, excipient, and propellant form a solution.

7. The medicinal aerosol composition of claim 1 wherein the drug and excipient form a suspension in the propellant.

8. The particulate medicinal composition of claim 6 wherein the drug and excipient form a hydrophobic ion pair complex.

9. The medicinal aerosol composition of claim 6 further comprising a cosolvent.

10. The medicinal aerosol composition of claim 1 wherein the excipient is present in an amount such that the period of therapeutic activity of the drug is increased by a factor of at least about 1.5 relative to the period of activity of the same composition with respect to the propellant and drug but without the excipient.

11. The medicinal aerosol composition of claim 1 wherein the molar ratio of excipient to drug is between about 1.5:1 and 1:2.

12. The medicinal aerosol composition of claim 10 wherein the molar ratio of excipient to drug is about 1:1.

* * * * *